(12) United States Patent
Paul

(10) Patent No.: US 7,038,591 B1
(45) Date of Patent: May 2, 2006

(54) APPARATUS FOR TESTING AND MARKING WORKPIECES

(76) Inventor: James A. Paul, 3908 Beverly Dr., Toledo, OH (US) 43614

(*) Notice: Subject to any disclaimer, the term of this patent is extended or adjusted under 35 U.S.C. 154(b) by 319 days.

(21) Appl. No.: 10/371,325

(22) Filed: Feb. 21, 2003

Related U.S. Application Data

(60) Provisional application No. 60/358,792, filed on Feb. 22, 2002.

(51) Int. Cl.
*G08B 21/00* (2006.01)

(52) U.S. Cl. .............................. 340/686.4; 340/686.5; 340/519; 340/539.24; 219/109; 219/121

(58) Field of Classification Search ............. 340/686.4, 340/686.5, 514, 515, 519, 524, 525, 542, 340/539.24; 219/109, 110, 121.62
See application file for complete search history.

(56) References Cited

U.S. PATENT DOCUMENTS

| | | | | |
|---|---|---|---|---|
| 4,896,170 A | * | 1/1990 | Niemeyer, III | 346/139 R |
| 5,188,047 A | * | 2/1993 | Rohr et al. | 112/470.03 |
| 5,254,828 A | * | 10/1993 | Stiebel | 219/110 |
| 5,288,968 A | * | 2/1994 | Cecil | 219/89 |
| 5,359,814 A | * | 11/1994 | Baltazar et al. | 451/5 |
| 5,614,109 A | * | 3/1997 | Cecil | 219/109 |
| 5,996,707 A | * | 12/1999 | Thome et al. | 173/2 |
| 6,046,677 A | * | 4/2000 | Kavanagh | 340/674 |
| 6,396,295 B1 | * | 5/2002 | Robinson et al. | 324/765 |
| 6,515,251 B1 | * | 2/2003 | Wind | 219/110 |

* cited by examiner

*Primary Examiner*—Jeffery Hofsass
*Assistant Examiner*—Daniel Previl
(74) *Attorney, Agent, or Firm*—MacMillan, Sobanski & Todd, LLC

(57) ABSTRACT

A workpiece testing and marking system includes an apparatus for testing a workpiece and for selectively generating a signal that is representative of a result of the test. The system also includes a marker that is adapted to provide a visual indication on the workpiece. A receptacle is provided for selectively supporting the marker. The receptacle includes a locking mechanism for selectively preventing removal of the marker from the receptacle. A controller is responsive to the test result signal for controlling the operation of locking mechanism. The locking mechanism can include a sensor for generating a signal to the controller when the marker is disposed within the receptacle. If the length of time that the marker is removed from the bore exceeds a predetermined maximum, then the controller can generate a fault or alarm signal to the operator of the testing apparatus.

20 Claims, 3 Drawing Sheets

APPARATUS FOR TESTING AND MARKING WORKPIECES

CROSS REFERENCE TO RELATED APPLICATION

This application claims the benefit of U.S. Provisional Application No. 60/358,792, filed Feb. 22, 2002, the disclosure of which is incorporated herein by reference.

BACKGROUND OF THE INVENTION

This invention relates in general to machines for testing and/or inspecting workpieces to insure that one or more predetermined standards of performance and/or quality have been met. In particular, this invention relates to an improved apparatus for testing such workpieces and for allowing an operator to manually mark such workpieces with a visually perceptible indication of the result of the testing, wherein the manual marking system minimizes the opportunities for an operator to apply an incorrect mark to the workpiece (i.e., mark a "good" workpiece as being "bad", or vice versa).

A variety of machines are known in the art for testing and/or inspecting workpieces to insure that one or more predetermined standards of performance and/or quality have been met. For example, in the manufacture of flexible conduits (such as rubber hoses) that convey pressurized fluids, it is often necessary or desirable to pressure test each and every hose that is manufactured to insure that it can withstand a predetermined amount of fluid pressure without leaking. To accomplish this, it is known to provide an apparatus including a source of pressurized fluid that communicates with a pair of couplings. To initiate a pressure test, the ends of the hose are connected to the couplings, and the source of pressurized fluid is energized so as to supply pressurized fluid within the hose for a predetermined period of time. If no leakage occurs during the course of the test, then the hose passes the pressure test and is satisfactory for use and/or sale. On the other hand, if some leakage occurs during the course of the test, then the hose fails the pressure test and is destroyed.

In order to prevent any confusion in distinguishing between the "good" workpieces that have passed the predetermined standard (such as the pressure test described above) and the "bad" hoses that have failed such standard, it is known to mark some of the workpieces with a visually perceptible indication. Typically, the visually perceptible indication is applied only to those "good" workpieces that have satisfied the predetermined standard, while the "bad" workpieces that have not satisfied the predetermined standard are left unmarked. However, in other instances, it may be desirable to mark the workpieces in the opposite manner, namely, apply the visually perceptible indication to the "bad" workpieces that have not satisfied the predetermined standard and leave the "good" workpieces that have satisfied the predetermined standard unmarked. Regardless, the use of a visually perceptible indication provides a clear and unambiguous mechanism for distinguishing between the workpieces that have passed the predetermined standard and those that have failed.

To facilitate the marking of the workpieces, a marking system is often provided in conjunction with or adjacent to the testing apparatus. A variety of such marking systems are known in the art. Some of such marking systems are mounted directly on the testing apparatus and function automatically to apply the visually perceptible indication to the "good" workpieces that have satisfied (or, alternatively, the "bad" workpieces that have not satisfied) the predetermined standard. However, the use of such automatic marking systems is not always feasible. For example, if the testing apparatus is used to test workpieces having a variety of sizes and shapes, or if the testing apparatus is used to test workpieces in a harsh or wet environment, then the use of an automatic marking system may be relatively difficult.

In these instances, a manual marking system (i.e., a marking system that is manually actuated by an operator of the testing apparatus to mark the workpieces after the testing has been completed) is often used. A typical manual marking system includes a marker that is manually used by the operator to apply the visually perceptible indication to the "good" workpieces that have satisfied (or, alternatively, to the "bad" workpieces that have not satisfied) the predetermined standard. Unfortunately, this simple approach is susceptible to errors (i.e., the incorrect marking of a "good" workpiece as being "bad", or vice versa) as a result of fatigue or carelessness on the part of the operator of the testing apparatus. Thus, it would be desirable to an improved apparatus for testing workpieces and for marking such workpieces with the visually perceptible indication that minimizes the opportunities for such errors to occur.

SUMMARY OF THE INVENTION

This invention relates to a manual marking system for providing tested workpieces with a visually perceptible indication of the result of the testing. The marking system includes a marker that is adapted to be moved into engagement with the tested workpiece and apply the appropriate visually perceptible indication thereto. A receptacle is provided for supporting the marker when not in use. The marker has a recessed area formed in the outer surface thereof that can cooperate with a locking mechanism contained within the receptacle to selectively lock the marker therein. The locking mechanism includes an actuator supported within the receptacle that includes a stationary member and a movable member. When it is desired to lock the marker in the receptacle, the actuator causes the movable member to move to an extended position, wherein a portion of the movable member extends into the recessed area formed on the marker. As a result, the marker is physically prevented from being removed from the receptacle. When it is desired to unlock the marker in the receptacle, the actuator causes the movable member to move to a retracted position, where the movable member is removed from the recessed area. As a result, the marker is free to be manually removed from the receptacle. The locking mechanism may, if desired, also include a sensor for generating a signal to a controller when the marker is disposed within the receptacle. If the length of time that the marker is removed from the bore exceeds a predetermined maximum, then the controller can generate a fault or alarm signal to the operator of the testing apparatus.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
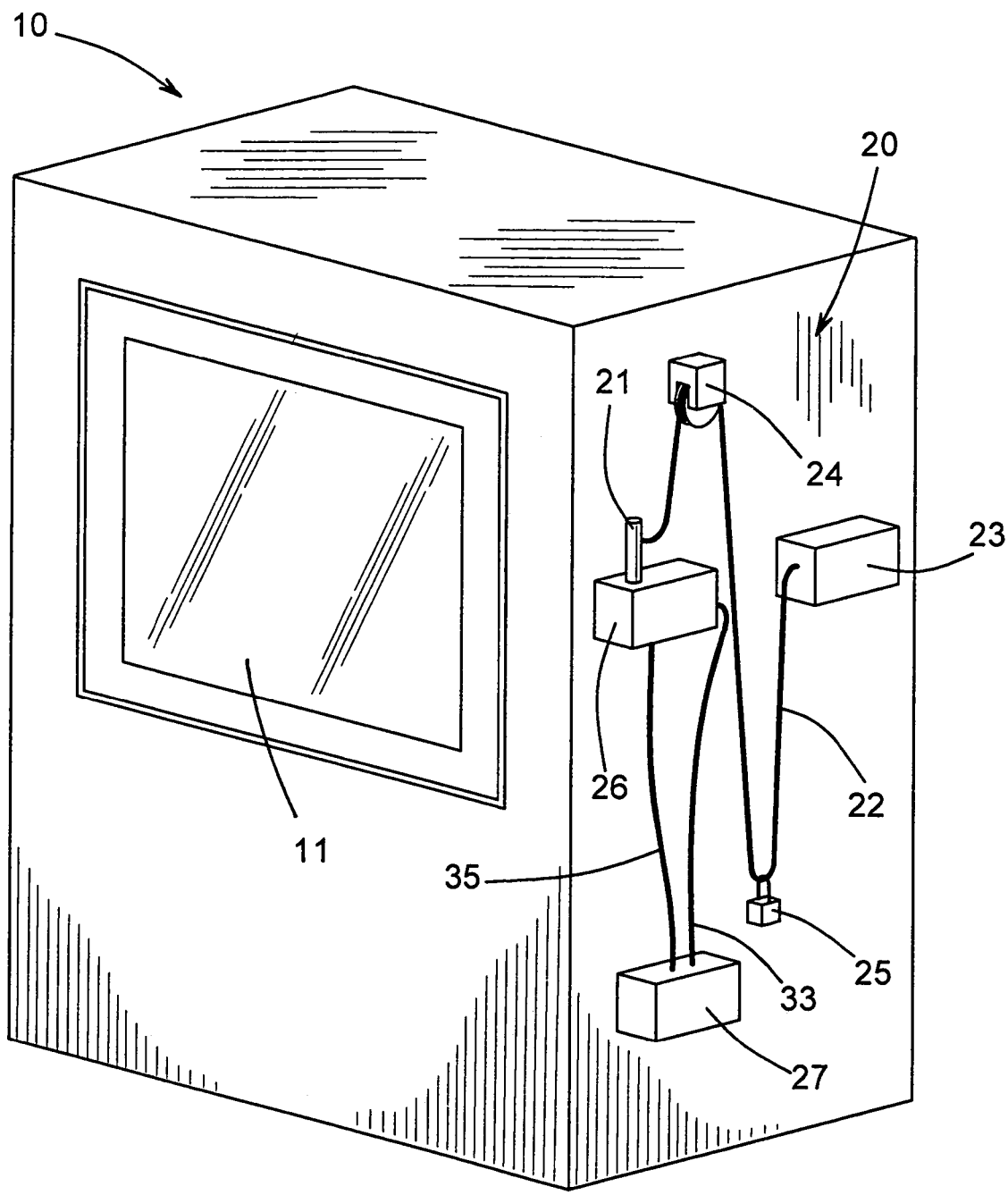
FIG. 1 is a schematic perspective view of a portion of an apparatus for testing and/or inspecting workpieces to insure that one or more predetermined standards of performance and/or quality have been met and a manual marking system for providing such workpieces with a visually perceptible indication of the result of the testing in accordance with this invention.

Referring now to the drawings, there is schematically illustrated in FIG. 1 a portion of an apparatus, indicated generally at 10, for testing and/or inspecting one or more workpieces (not shown) to insure that one or more predetermined standards of performance and/or quality have been met. The illustrated testing apparatus 10 is designed to pressure test flexible conduits (such as rubber hoses) in the manner described above. To accomplish this, the illustrated testing apparatus 10 includes a hinged door 11 that provides selective access to an internal testing chamber (not shown). When the door 11 is opened, one or more workpieces can be installed within the internal chamber for testing or removed therefrom after testing. When the door 11 is closed, the testing process can occur in the manner described above while contained within a controlled environment. Although this invention will be described in the context of the illustrated pressure testing apparatus, it will be appreciated that this invention may be practiced in conjunction with any type of apparatus or machine for testing and/or inspecting any type of workpieces or, for that matter, for performing any other desired function on or in conjunction with such workpieces, for which it may be necessary or desirable to provide a visual indication on some or all of the workpieces as a result thereof. Thus, it will be appreciated that the illustrated testing apparatus 10 is intended to be representative of any such type of apparatus or machine.

A manual marking system, indicated generally at 20, is supported on the side of the testing apparatus 10 for providing the tested workpieces with a visually perceptible indication of the result of the testing. The marking system 20 includes a marker 21 that is adapted to be moved into engagement with the tested workpiece and apply the appropriate visually perceptible indication thereto. In this regard, the marker 21 is generally conventional in the art and may, for example, be embodied as a paint pen that communicates through a flexible conduit 22 with a source of paint 23. However, as will become apparent from the description below, this invention can be used with any type of marker or, for that matter, any other type of selectively usable device. The flexible conduit 22 is preferably sufficiently lengthy as to allow it to easily extend within the internal chamber of the testing apparatus 10 to apply the visually perceptible indication to the appropriate workpieces therein following testing. To facilitate the orderly retraction of the marker 21 and the flexible conduit 22 when not in use, the flexible conduit 22 may include a first portion that extends over a pulley 24 supported on the side of the testing apparatus 10 and a second portion that carries a counterweight 25 thereon. The pulley 24 and the counterweight 25 function to return the flexible conduit 22 to a retracted position adjacent to the side of the testing apparatus 10 in an orderly manner when the marker 21 is not in use.

A receptacle 26 is provided for supporting the marker 21 when not in use. In the illustrated embodiment, the receptacle 26 is supported on the side of the testing apparatus 10, although such is not necessary. In a manner that is described in detail below, the receptacle 26 includes a mechanism for selectively locking the marker 21 therein to prevent removal therefrom, except under predetermined circumstances. To control this locking mechanism, a controller 27 is provided. In the illustrated embodiment, the controller 27 is an electronic controller that is also supported on the side of the testing apparatus 10, although such is not necessary. The operation of the controller 27 will also be explained in detail below.

Figure 2:
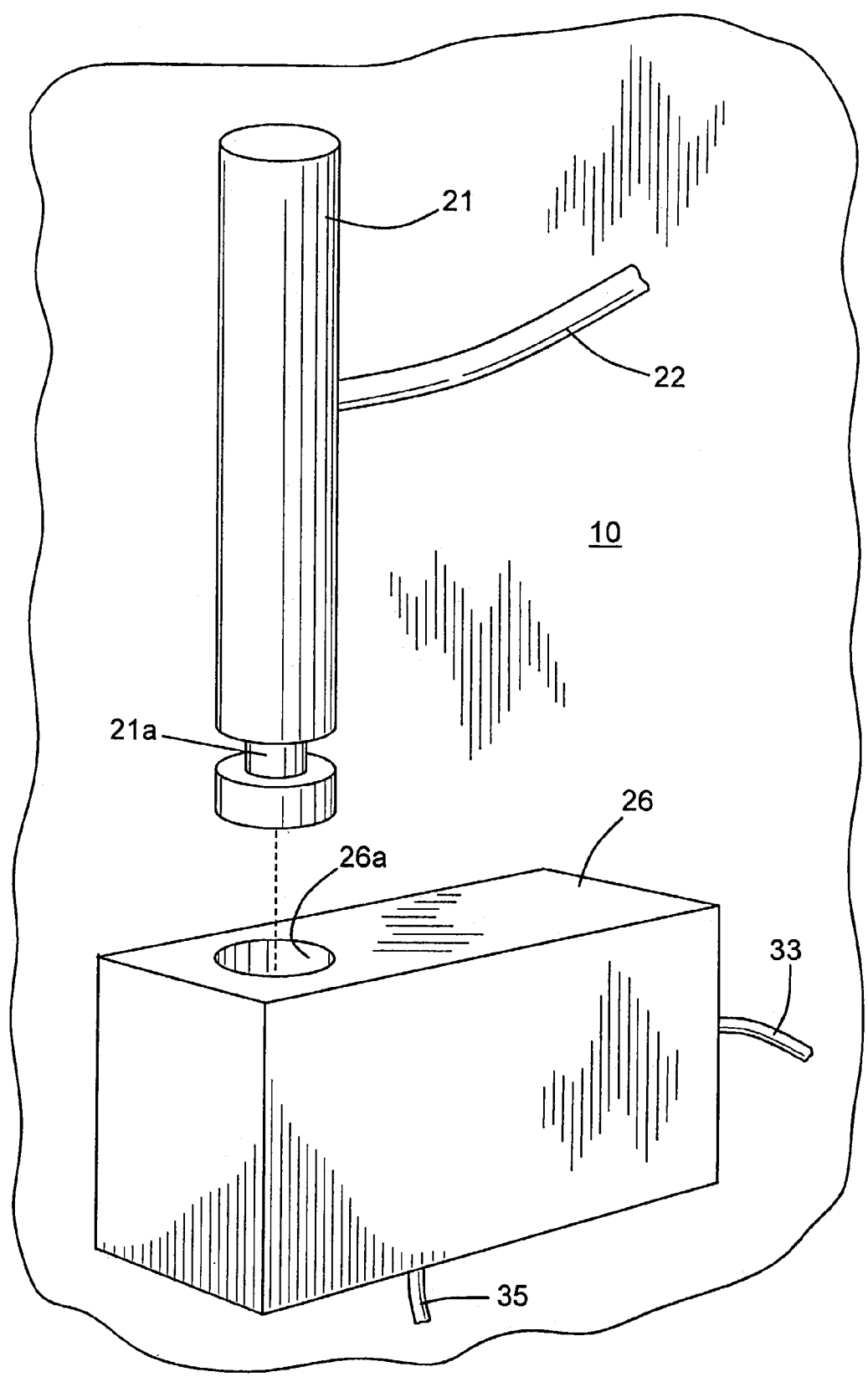
FIG. 2 is an enlarged perspective view of a portion of the manual marking system illustrated in FIG. 1.

Referring now to FIG. 2, the structures of the marker 21 and the receptacle 26 are illustrated in more detail. As shown therein, the marker 21 has a recessed area 21a formed in the outer surface thereof. In the illustrated embodiment, the recessed area 21a is an annular groove that extends completely about the marker 21. However, the recessed area 21a may be embodied as any space or structure that can cooperate with the locking mechanism contained within the receptacle 26 to selectively lock the marker 21 therein. A bore 26a is formed in the receptacle 26 for selectively receiving the marker 21 therein. The bore 26a is preferably sized and shaped to facilitate the easy installation and removal of the marker 21. Thus, in the illustrated embodiment, the marker 21 has a cylindrical outer surface defining an outer diameter, and the bore 26a (which extends generally vertically) has a cylindrical inner surface that defines an inner diameter that is slightly larger than the outer diameter of the marker 21.

Figure 3:
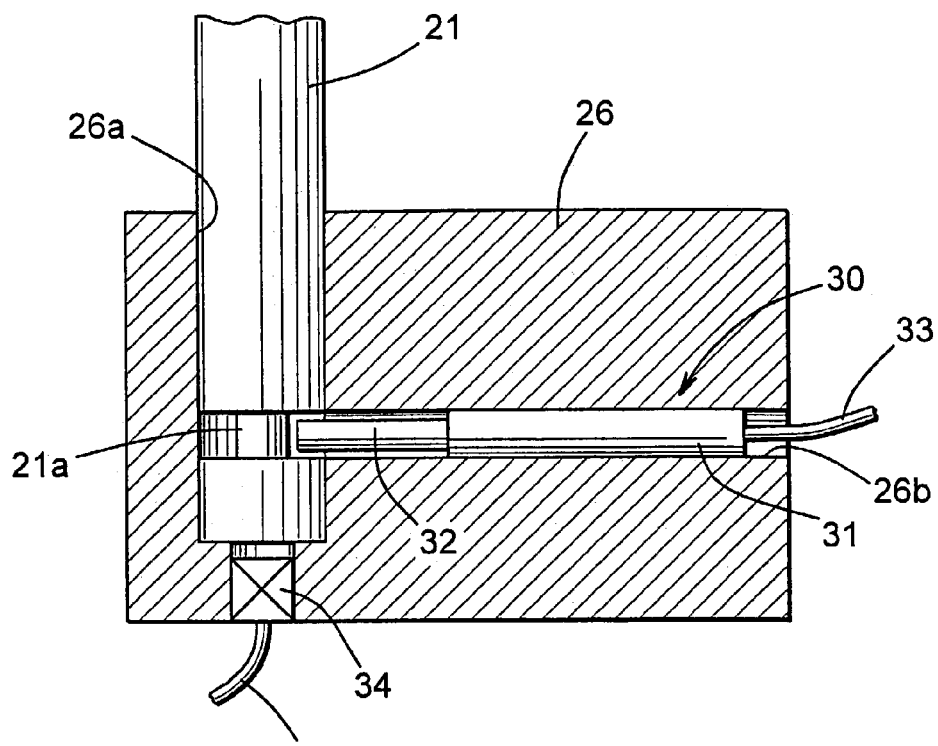
FIG. 3 is a sectional elevational view of the portion of the manual marking system illustrated in FIGS. 1 and 2 showing a marker locking mechanism in a locked position.
Figure 4:
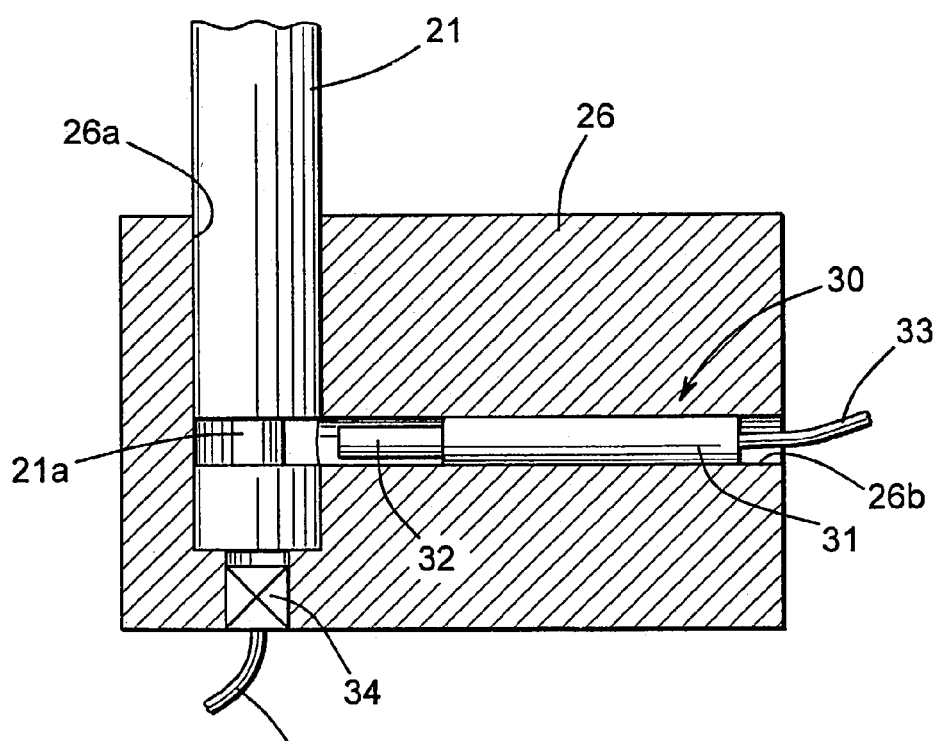
FIG. 4 is a sectional elevational view similar to FIG. 3 showing the marker locking mechanism in an unlocked position.

Referring now to FIGS. 3 and 4, the operation of the locking mechanism in the receptacle 26 is illustrated in detail. As shown therein, the locking mechanism includes an actuator, indicated generally at 30, that is disposed in a transverse bore 26b formed in the receptacle 26. The actuator 30 includes a stationary member 31 and a movable member 32. The stationary member 31 is preferably press fit or otherwise supported in the transverse bore 26b so as to be fixed in position relative to the receptacle 26. The movable member 32 is supported within the stationary member 31 for movement between an extended position (illustrated in FIG. 3) and a retracted position (illustrated in FIG. 4). The actuator 30 can be embodied as any conventional device, such as a solenoid, pneumatic, or hydraulic actuator, for selectively causing this extending and retracting movement of the movable member 32 relative to the stationary member 31. The operation of the actuator 30 can be controlled by the controller 27 by means of a control line 33 extending therebetween or any other conventional means.

As shown in FIG. 3, when it is desired to lock the marker 21 in the receptacle 26, the actuator 30 is actuated by the controller 27 to move the movable member 32 to the extended position. When this occurs, a portion of the movable member 32 extends into the recessed area 21a formed on the marker 21. As a result, the marker 21 is physically prevented from being removed from the bore 26a formed in the receptacle 26. On the other hand, as shown in FIG. 4, when it is desired to unlock the marker 21 in the receptacle 26, the actuator 30 is actuated by the controller 27 to move the movable member 32 to the retracted position. When this occurs, the movable member 32 is removed from the recessed area 21a formed on the marker 21. As a result, the marker 21 is free to be manually removed from the bore 26a formed in the receptacle 26.

The locking mechanism may, if desired, also include a sensor 34 for generating a signal to the controller 27 when the marker 21 is disposed within the bore 26a formed through the receptacle 26. The sensor 34 may be embodied as any conventional sensing device, such as the illustrated electronic proximity sensor, a mechanical limit switch, and the like. The signal from the sensor 34 may be delivered to the controller 27 by means of a control line 35 extending therebetween or any other conventional means. The purpose for providing the sensor 34 will be described below.

The operation of the testing apparatus 10 and the manual marking system 20 will now be explained. Initially, the marker 21 is stored within the bore 26*a* formed through the receptacle 26, and the controller 27 generates a signal to the actuator 30 to move the movable member 32 to the extended position illustrated in FIG. 3. As a result, the marker 21 is locked to the receptacle 26 and cannot be removed therefrom. Also, the sensor 34 generates a signal to the controller 27 confirming that the marker 21 is, in fact, disposed within the bore 26*a*. Then, one or more workpieces are installed within the testing apparatus 10 and tested in a conventional manner, such as described above. The controller 27 may, if desired, be programmed to operate the various components of the testing apparatus 10 to conduct the test. Alternatively, a separate controller (not shown) may be programmed to operate the various components of the testing apparatus 10 to conduct the test, and the controller 27 may be configured to merely receive a signal from this other controller when the test is concluded. At the end of the test, a signal is generated by or to the controller 27 that is representative of the results of the test, i.e., whether the predetermined standard or standards of performance and/or quality of the workpiece have been met.

In either event, at the conclusion of the test, it is desirable for the operator of the testing apparatus 10 to mark certain ones of the workpieces with an appropriate visually perceptible indication, as described above. For the sake of illustration, let it be assumed that it is desirable for the operator of the testing apparatus 10 to apply the visually perceptible indication only to those "good" workpieces that have satisfied the predetermined standard, while the "bad" workpieces that have not satisfied the predetermined standard are left unmarked. If, at the conclusion of the test, none of the workpieces has satisfied the predetermined standard (i.e., are "bad" workpieces), then the controller 27 continues to generate the signal to the actuator 30 to maintain the movable member 32 in the extended position illustrated in FIG. 3. As a result, the marker 21 continues to be locked to the receptacle 26 and cannot be removed therefrom. This locking of the marker 21 prevents any of the "bad" workpieces from inadvertently being marked as "good" workpieces. Thus, all of such "bad" workpieces are removed from the testing apparatus 10, and a new group of workpieces is inserted therein for testing.

If, on the other hand, at the conclusion of the test, some or all of the workpieces have satisfied the predetermined standard (i.e., are "good" workpieces), then the controller 27 generates a signal to the actuator 30 to move the movable member 32 from the extended position illustrated in FIG. 3 to the retracted position illustrated in FIG. 4. As a result, the marker 21 is unlocked from the receptacle 26. Thus, the operator of the testing apparatus 10 can remove the marker 21 from the receptacle 26 and, in the manner described above, manually apply the visually perceptible indication to the appropriate workpieces contained within the testing apparatus 10. While the marker 21 is removed from the receptacle 26 to mark the "good" parts, the sensor 34 generates a signal to the controller 27 indicating that the marker 21 is no longer disposed within the bore 26*a*. Thereafter, when the operator has completed such marking of the workpieces contained within the testing apparatus 10, the marker 21 is re-inserted within the bore 26*a* formed through the receptacle 26. When this occurs, the sensor 34 generates a signal to the controller 27 indicating that the marker 21 is again disposed within the bore 26*a*. The controller 27 can be responsive to this signal from the sensor 34 for generating the signal to the actuator 30 to move the movable member 32 back to the extended position illustrated in FIG. 3. As a result, the marker 21 is again locked to the receptacle 26 and cannot be removed therefrom until the next test cycle is completed. Lastly, the marked (and unmarked, if any) workpieces are removed from the testing apparatus 10, and a new group of workpieces is inserted therein for testing.

As mentioned above, while the marker 21 is removed from the receptacle 26 to mark the "good" parts, the sensor 34 generates a signal to the controller 27 indicating that the marker 21 is no longer disposed within the bore 26*a*. The controller 27 can be programmed to measure the amount of time that the marker 21 is removed from the receptacle 26 while the operator is marking the workpieces. If the length of time that the marker 21 is removed from the bore 26*a* exceeds a predetermined maximum, then the controller 27 can generate a fault or alarm signal to the operator of the testing apparatus 10. The purpose of this fault or alarm signal is to motivate the operator to quickly apply the visually perceptible indication to the appropriate workpieces contained within the testing apparatus 10, then immediately return the marker 21 to the receptacle 26. This time-out provision prevents the marker 21 from being damaged as a result of improper storage after each use, and further minimizes the opportunity of the operator to inadvertently or deliberately pre-mark workpieces before testing. Thus, the safety and reliability of the testing apparatus 10 and the manual marking system 20 are enhanced.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

The invention claimed is:

1. A workpiece testing and marking system comprising:
   an apparatus for testing a workpiece and for selectively generating a signal that is representative of a result of the test;
   a marker that is adapted to provide a visual indication on the workpiece, said marker having a recessed area formed therein;
   a receptacle for selectively supporting said marker, said receptacle including a locking mechanism for selectively preventing removal of said marker from said receptacle, a portion of said locking mechanism selectively extending into said recessed area to prevent removal of said marker from said receptacle; and
   a controller that is responsive to said test result signal for controlling the operation of said locking mechanism.

2. The workpiece testing and marking system defined in claim 1 wherein said receptacle has a bore formed therein for selectively receiving said marker.

3. The workpiece testing and marking system defined in claim 1 wherein said locking mechanism includes an actuator having a stationary member and a movable member slidably supported in said stationary member, wherein said movable member selectively engages said marker to prevent removal of said marker from said receptacle.

4. The workpiece testing and marking system defined in claim 1 wherein said marker has a recessed area formed therein, said locking mechanism includes an actuator having a stationary member and a movable member slidably supported in said stationary member, and said movable member selectively extends into said recessed area to prevent removal of said marker from said receptacle.

5. The workpiece testing and marking system defined in claim 4 wherein said controller generates a signal if said marker is removed from said receptacle for longer than predetermined period of time.

6. The workpiece testing and marking system defined in claim 1 further including a sensor that generates a signal to said controller when said marker is supported on said receptacle.

7. The workpiece testing and marking system defined in claim 1 wherein said control unit engages said locking mechanism when said marker is supported in said receptacle until said testing apparatus generates said signal.

8. The workpiece testing and marking system defined in claim 1 wherein said receptacle and said control unit are mounted on said testing device.

9. The method defined in claim 1 wherein said step (d) is performed by causing the control unit to engage the locking mechanism when the marker is supported in the receptacle until the testing apparatus generates the signal.

10. A method of testing and marking a workpiece comprising the steps of:
   (a) providing an apparatus for testing a workpiece and for selectively generating a signal that is representative of a result of the test;
   (b) providing a marker having a recessed area formed therein that is adapted to provide a visual indication on the workpiece;
   (c) providing a receptacle for selectively supporting the marker, wherein the receptacle includes a locking mechanism with a portion that selectively extends into the recessed area for selectively preventing removal of the marker from the receptacle; and
   (d) controlling the operation of said locking mechanism in response to the test result signal.

11. The method defined in claim 10 wherein said step (c) is performed by providing a receptacle having a bore formed therein for selectively receiving the marker.

12. The method defined in claim 10 wherein said step (c) is performed by providing a locking mechanism including an actuator having a stationary member and a movable member slidably supported in the stationary member, wherein the movable member selectively engages the marker to prevent removal of the marker from the receptacle.

13. The method defined in claim 10 including the further step of providing a sensor that generates a signal to the controller when the marker is supported on the receptacle.

14. The method defined in claim 13 wherein the controller generates a signal if the marker is removed from the receptacle for longer than predetermined period of time.

15. A workpiece testing and marking system comprising:
   an apparatus for testing a workpiece and for selectively generating a signal that is representative of a result of the test;
   a marker that is adapted to provide a visual indication on the workpiece;
   a receptacle for selectively supporting said marker, said receptacle including a locking mechanism for selectively preventing removal of said marker from said receptacle, said locking mechanism including an actuator having a stationary member and a movable member slidably supported in said stationary member, wherein said movable member selectively engages said marker to prevent removal of said marker from said receptacle; and
   a controller that is responsive to said test result signal for controlling the operation of said locking mechanism.

16. The workpiece testing and marking system defined in claim 15 wherein said marker has a recessed area formed therein, and wherein said movable member selectively extends into said recessed area to prevent removal of said marker from said receptacle.

17. The workpiece testing and marking system defined in claim 15 wherein said receptacle has a bore formed therein for selectively receiving said marker.

18. The workpiece testing and marking system defined in claim 15 further including a sensor that generates a signal to said controller when said marker is supported on said receptacle.

19. The workpiece testing and marking system defined in claim 15 wherein said controller generates a signal if said marker is removed from said receptacle for longer than predetermined period of time.

20. The workpiece testing and marking system defined in claim 15 wherein said control unit engages said locking mechanism when said marker is supported in said receptacle until said testing apparatus generates said signal.

* * * * *